United States Patent [19]

Momany

[11] Patent Number: 4,880,777

[45] Date of Patent: Nov. 14, 1989

[54] SYNTHETIC PEPTIDES HAVING GROWTH HORMONE RELEASING ACTIVITY

[75] Inventor: Frank A. Momany, Concord, Mass.

[73] Assignee: Eastman Kodak Company, Rochester, N.Y.

[21] Appl. No.: 91,919

[22] Filed: Sep. 1, 1987

[51] Int. Cl.[4] ................... A61K 37/43; C07K 7/10
[52] U.S. Cl. ................................ 514/12; 530/324
[58] Field of Search ........................ 514/12; 530/324

[56] References Cited

U.S. PATENT DOCUMENTS

| | | | |
|---|---|---|---|
| 4,105,603 | 8/1978 | Vale, Jr. et al. | 260/8 |
| 4,127,517 | 11/1978 | Coy et al. | 260/8 |
| 4,127,519 | 11/1978 | Coy et al. | 260/8 |
| 4,127,520 | 11/1978 | Coy et al. | 260/8 |
| 4,127,521 | 11/1978 | Coy et al. | 260/8 |
| 4,127,522 | 11/1978 | Coy et al. | 260/8 |
| 4,127,523 | 11/1978 | Coy et al. | 260/8 |
| 4,127,524 | 11/1978 | Coy et al. | 260/8 |
| 4,127,525 | 11/1978 | Coy et al. | 260/8 |
| 4,127,526 | 11/1978 | Coy et al. | 260/8 |
| 4,127,527 | 11/1978 | Coy et al. | 260/8 |
| 4,127,528 | 11/1978 | Coy et al. | 260/8 |
| 4,127,529 | 11/1978 | Coy et al. | 260/8 |
| 4,127,530 | 11/1978 | Coy et al. | 260/8 |
| 4,127,532 | 11/1978 | Coy et al. | 260/8 |
| 4,127,533 | 11/1978 | Coy et al. | 260/8 |
| 4,127,536 | 11/1978 | Coy et al. | 260/8 |
| 4,127,537 | 11/1978 | Coy et al. | 260/8 |
| 4,127,538 | 11/1978 | Coy et al. | 260/8 |
| 4,127,539 | 11/1978 | Coy et al. | 260/8 |
| 4,127,540 | 11/1978 | Coy et al. | 260/8 |
| 4,127,541 | 11/1978 | Coy et al. | 260/8 |
| 4,139,504 | 2/1979 | Coy et al. | 260/8 |
| 4,178,284 | 12/1979 | Sarantakis | 260/112.5 |
| 4,223,019 | 9/1980 | Momany | 424/177 |
| 4,223,020 | 9/1980 | Momany | 424/177 |
| 4,223,021 | 9/1980 | Momany | 424/177 |
| 4,224,316 | 9/1980 | Momany | 424/177 |
| 4,226,857 | 10/1980 | Momany | 424/177 |
| 4,228,155 | 10/1980 | Momany | 424/177 |
| 4,228,157 | 10/1980 | Momany | 424/177 |
| 4,228,158 | 10/1980 | Momany | 424/177 |
| 4,312,857 | 1/1982 | Coy et al. | 424/177 |
| 4,410,512 | 10/1983 | Bowers | 424/177 |
| 4,410,513 | 10/1983 | Momany | 424/177 |
| 4,411,890 | 10/1983 | Momany | 424/177 |
| 4,491,541 | 1/1985 | de Castiglione et al. | 260/112.5 |
| 4,505,897 | 3/1985 | Coy et al. | 514/11 |
| 4,508,711 | 4/1985 | Coy et al. | 514/11 |
| 4,517,181 | 5/1985 | Ling et al. | 514/12 |
| 4,518,586 | 5/1985 | Rivier et al. | 514/12 |
| 4,528,190 | 7/1985 | Vale, Jr. et al. | 514/12 |
| 4,529,595 | 7/1985 | Rivier et al. | 514/12 |
| 4,562,175 | 12/1985 | Chang et al. | 514/12 |
| 4,563,352 | 1/1986 | Rivier et al. | 514/12 |
| 4,585,756 | 4/1986 | Brazeau, Jr. et al. | 514/12 |
| 4,595,676 | 6/1986 | Spiess et al. | 514/12 |
| 4,605,643 | 8/1986 | Bohlen et al. | 514/12 |
| 4,610,976 | 9/1986 | Bohlen et al. | 514/12 |
| 4,617,149 | 10/1986 | DiMarchi et al. | 530/324 |
| 4,622,312 | 11/1986 | Felix et al. | 514/12 |
| 4,626,523 | 12/1986 | Vale, Jr. et al. | 514/12 |
| 4,628,043 | 12/1986 | Spiess et al. | 514/12 |
| 4,649,131 | 3/1987 | Felix et al. | 514/12 |

Primary Examiner—Delbert R. Phillips
Attorney, Agent, or Firm—S. E. Reiter; William P. Heath, Jr.

[57] ABSTRACT

Disclosed are novel polypeptides selected from the group consisting of:

Compound 1
Tyr—Ala—Asp—Ala—Ile—Phe—Thr—Asn—Cys—Tyr—Arg—

Lys—Val—Leu—Cys—Gln—Leu—Ser—Ala—Arg—Lys—Leu—

Leu—Gln—Asp—Ile—Nle—Ser—Arg—$NH_2$ (free dithiol);

functional equivalents thereof:
and organic and inorganic addition salts thereof; and Compound 2
Tyr—Ala—Asp—Ala—Ile—Phe—Thr—Asn—Cys—Tyr—Arg—

Lys—Val—Leu—Cys—Gln—Leu—Ser—Ala—Arg—Lys—Leu—

Leu—Gln—Asp—Ile—Nle—Ser—Arg—$NH_2$ (cyclic disulfide);

functional equivalents thereof:
and organic and inorganic addition salts thereof.

These polypeptides have been found to promote the release and elevation of growth hormone levels in the blood of animals. Also disclosed are novel combinations of said polypeptides with other polypeptides, novel formulations including said polypeptides as well as methods for administering said polypeptides, alone and in combination with other polypeptides acting in a synergistic manner to promote release and elevation of growth hormone levels in animals.

12 Claims, No Drawings

SYNTHETIC PEPTIDES HAVING GROWTH HORMONE RELEASING ACTIVITY

FIELD OF THE INVENTION

This invention relates to novel synthetic polypeptides possessing growth hormone releasing activity. The invention is also directed to combinations of polypeptides which act synergistically to promote the release and elevation of growth hormone levels in animals.

DESCRIPTION OF THE PRIOR ART

It is known that an increase in the level of circulating growth hormones can cause mammals to have faster growth rates and increased milk production (P. K. Baker et al., *J. Animal Science* 59 (Supplement 1), 220 (1984); W. J. Croom, et al., *J. Diary Sci.* 67 (Supplement 1), 109 (1984); S. N. McClutcheon et al., *J. Dairy Sci.* 67, 288 (1984)).

Various ways are known for promoting the release of growth hormone. For instance, the existence of natural or endogenous growth hormone releasing factors have been established. See, for example, the naturally occurring growth hormone releasing factors described in P. Brazeau et al., *Proc. Natl. Acad. Sci. USA* 79, 7909 (1982) and M. O. Thorner et al., *Lancet* 1, 24 (1983). In addition, certain chemically defined polypeptides promote the release of growth hormone either by acting directly on the pituitary or indirectly as by acting on the hypothalamus. Illustrative of such polypeptides are the Group 2 compounds described hereinafter (C. Y. Bowers et al., *Endocrinology* 114, 1537 (1984), F. A. Momany et al., *Endocrinology* 114, 1531 (1984) and C. Y. Bowers, 7th *International Congress of Endocrinology Abstracts*, 464 (1984). Other recently discovered polypeptide growth hormone releasing factors have been described in Tori et al., *Biochemical and Biophysical Research Communications* 139, 763 (1986) and Velicelebi et al., *Proc. Natl. Acad. Sci. USA* 83, 5397 (1986).

Antibodies to the endogenous growth hormone release inhibitor, somatostatin (SRIF) have also been used to elevate GH levels. (W. B. Wehrenberg et al., *Endocrinology* 115, 1218 (1984)). Finally, it has been shown that some compounds such as morphine (C. Rivier et al., *Endocrinology* 100, 238 (1977)) and other alkaloids (C. Y. Bowers, *Endocrinology* 117, 1441 (1985)) and DAla$^2$, DLeu-enkephalinamide (E. L. Lien et al., *FEBS Letters* 88, 208 (1978)) also promote the release of growth hormone.

SUMMARY OF THE INVENTION

It is an object of this invention to provide novel growth hormone releasing peptides.

It is also an object of this invention to provide a method for elevating GH levels in mammals.

Another object of the invention is to provide a combination of the novel growth hormone releasing compounds and other defined peptides which give a synergistic effect in elevating GH levels in vivo.

These and other objects of the invention are achieved by novel polypeptides selected from the group consisting of:

Compound 1
Tyr—Ala—Asp—Ala—Ile—Phe—Thr—Asn—Cys—Tyr—Arg—

Lys—Val—Leu—Cys—Gln—Leu—Ser—Ala—Arg—Lys—Leu—

Leu—Gln—Asp—Ile—Nle—Ser—Arg—NH$_2$ (free dithiol), functional equivalents thereof, and organic and inorganic addition salts thereof, and Compound 2
Tyr—Ala—Asp—Ala—Ile—Phe—Thr—Asn—Cys—Tyr—Arg—

Lys—Val—Leu—Cys—Gln—Leu—Ser—Ala—Arg—Lys—Leu—

Leu—Gln—Asp—Ile—Nle—Ser—Arg—NH$_2$ (cyclic disulfide), functional equivalents thereof, and organic and inorganic addition salts thereof.

In another embodiment of the invention, there are provided combinations capable of promoting the release of growth hormone comprising an effective amount of (i) at least one polypeptide selected from the group consisting of:
Tyr-Ala-Asp-Ala-Ile-Phe-Thr-Asn-Cys-Tyr-Arg-Lys-Val-Leu-Cys-Gln-Leu-Ser-Ala-Arg-Lys-Leu-Leu-Gln-Asp-Ile-Nle-Ser-Arg-NH$_2$ (free dithiol), functional equivalents thereof, and organic and inorganic addition salts thereof, and
Tyr-Ala-Asp-Ala-Ile-Phe-Thr-Asn-Cys-Tyr-Arg-Lys-Val-Leu-Cys-Gln-Leu-Ser-Ala-Arg-Lys-Leu-Leu-Gln-Asp-Ile-Nle-Ser-Arg-NH$_2$ (cyclic disulfide), functional equivalents thereof, and organic and inorganic addition salts thereof; and (ii) at least one polypeptide selected from the group consisting of: the Group 2 polypeptides and Group 3 polypeptides, described below, and organic and inorganic addition salts thereof, and mixtures of any two or more of such polypeptides, in a ratio such that, such combinations synergistically promote the release and elevation of growth hormone levels in the blood of an animal.

The term "functional equivalents thereof" as employed in this specification is intended to refer to both Compounds 1 and 2, as well as related compounds which retain substantially similar biological activity, e.g., the ability to promote the release of growth hormone in the animal being treated, enhance milk production in cows, enhance body growth in animals such as mammals (e.g., humans, sheep, bovine and swine), as well as fish, fowl and crustaceans; and increase wool and/or fur production in mammals. Functional equivalents include compounds which differ from the recited structures by the addition of one or more amino acids to produce a longer chain peptide, e.g., additions to the C-terminus to incorporate naturally occurring GRF sequences, such as, for example, porcine, bovine, ovine, human and rat; compounds to which one or more of the designated amine acids are replaced with other L or D amino acids or related organic acids, amines, amides or the like; compounds which contain side chain modifications and/or functional groups on the terminal amino acids, so long as the presence of the functional groups does not interfere with the desired biological activity.

The term "synergistic", as used in this specification and the appended claims, means that when the novel Compounds 1 and 2 described herein are administered in combination with Group 2 and/or Group 3 compounds, the combination promotes the release of much more GH than is predicted by the summation of the individual responses for each component of the combination.

The invention is also concerned with a method of promoting release of growth hormone and consequent elevation of growth of hormone levels in the blood of an animal comprising administering to the animal an effective amount of a polypeptide selected from the novel Compounds 1 and 2 of the invention and mixtures thereof or a synergistic combination of at least one of Compounds 1 and 2 with at least one of the Group 2 or Group 3 polypeptides described below.

DETAILED DESCRIPTION OF THE INVENTION

The novel Compounds 1 and 2 of the invention, and functional equivalents thereof, can be synthesized according to the usual methods of solution and solid phase peptide chemistry, or by classical methods known in the art. The solid-phase synthesis is commenced from the C-terminal end of the peptide. A suitable starting material can be prepared, for instance, by attaching the required protected α-amino acid to a benzhydrylamine (BHA) resin, or a p-methylbenzylhydrylamine (p-MeBHA) resin. The BHA resin has been described by Pietta and Marshall, *Chem. Commn.*, 650 (1970) and is commercially available from Penninsula Laboratories, Inc., Belmont, Calif.

After the initial attachment, the α-amino protecting group can be removed by a choice of reagents, including trifluoroacetic acid (TFA) or hydrochloric acid (HCl) solutions in organic solvents at room temperature. After removal of the α-amino protecting group, the remaining protected amino acids can be coupled stepwise in the desired order. Each protected amino acid can be generally reacted in about a 3-fold excess using an appropriate carboxyl group activator such as dicylohexylcarbodiimide (DCC) in solution, for example, in methylene chloride ($CH_2Cl_2$) or N,N-dimethylformamide (DMF) and mixtures thereof.

After the desired amino acid sequence has been completed, the desired peptide can be cleaved from the solid phase resin support by treatment with a reagent such as hydrogen fluoride (HF) which not only cleaves the peptide from the resin, but also cleaves most commonly used side-chain protecting groups. When the BHA or p-Me-BHA resin is used, HF treatment results directly in free peptide amides.

Once the appropriate sequence of amino acids has been assembled, cleavage of the peptide from the resin, and removal of the protecting groups provides the desired novel Compound 1. Cyclic disulfide novel Compound 2 can be obtained from Compound 1 (free dithiol) as follows:

Following cleavage of the peptide fragment from the resin and removal of the protecting groups from the side chains of the cysteines, the linear polypeptide is cyclized to the disulfide linked analog via oxidation. This oxidation may be performed by dissolving the peptide in a large excess of water, adjusting the pH to approximately 8 with dilute caustic and oxidizing with a suitable oxidizing agent. The oxidizing agent of choice is potassium ferricyanide, but other oxidizing agents can be used or oxygen can be bubbled through the peptide-containing solution as well. If potassium ferricyanide is used, excess ferro- and ferricyanide ions can be removed with a weakly basic polyamide ion exchange resin, such as, for example, Rexyn 203 ($Cl^-$ Form).

The solid-phase procedure described above is well known in the art and has been described by Stewart and Young, *Solid Phase Peptide Synthesis:* (Second Edn., Pierce Chemical Co., Rockford, Il. (1984)).

Some of the well known solution methods which can be employed to synthesize the peptide moieties of the instant invention are set forth in Bodansky et al, *Peptide Synthesis*, 2nd Edition, John Wiley & Sons, New York, N.Y. (1976).

The desired peptide moieties can be obtained in substantially pure form by employiing any of a variety of methods readily available to those of skill in the art, such as, for example, high pressure liquid chromatography, low pressure liquid chromatography, precipitation, counter-current extraction, crystallization/recrystallization, and the like.

The novel Compounds 1 and 2 of the invention have also been found to be synergistic in combination with at least one of the compounds of the Group 2 or 3 polypeptides set forth below and can be administered to animals in effective amounts sufficient to promote release of growth hormone in vivo. For example, the novel Compound 1 and/or Compound 2 or combinations thereof with the Group 2 and/or Group 3 polypeptides can be administered to treat symptoms related to growth hormone deficiencies, increase body growth in humans and meat-producing animals such as sheep, bovines and swine, enhance milk, fur or wool production and the like.

Group 2 polypeptides which may be combined with the novel Compound 1 and/or Compound 2 of the invention, or functional equivalents thereof, to provide a synergistic effect (optionally in further combination with a Group 3 polypeptide as described hereinafter) are selected from any of polypeptides having the structure:

A-AA1-AA2-AA-3-AA4-Trp-AA6-AA7-Z, wherein

X is selected from the group consisting of H, DOPA, Lys, Phe, Tyr, Cys, Tyr-DAla-Phe-Gly, Tyr-DAla-Gly-Phe and Tyr-Ala-Gly-Thr;

AA1 is selected from the group consisting of H, all naturally occurring L-amino acids, as well as Met(O), DOPA and Abu;

AA2 is selected from the group consisting of His and 3(NMe)His (i.e., wherein the imidazole ring is methylated at the 3-position);

AA3 is selected from the group consisting of DTrp; 5-fluoro-D or D/LTrp; 6-fluoro-D or D/LTrp (i.e., wherein the indole ring is fluorinated at the 5- or 6-position); formyl)DTp (i.e., DTrp which is formylated at the indole nitrogen); *XTrp, wherein *XTrp is selected from the group consisting of the N-monomethylated DTrp isomers (i.e., ($N^\alpha$Me)DTrp and (indole NMe)DTrp); $D^\alpha$Nal; and $D^\beta$Nal;

AA4 is selected from the group consisting of Ala, Gly and Ser;

AA6 is selected from the group consisting of DPhe and (NMe)DPhe;

AA7 is selected from the group consisting of Arg, iLys, Lys and Orn; and

Z represents the C terminal end group of said polypeptide or the C terminal amino acid(s) plus end group, wherein Z is selected from the group consisting of —$CONH_2$, —COOH, —COOR, —CONHR, —$CONR_2$, —$CH_2OH$ and —$CH_2OR$, wherein each R is independently an alkyl group having 1–6 carbon atoms or an aromatic ring having up to 12 carbon atoms; and wherein Z is alternatively selected from the group consisting of -Gly-Z', -Met-Z', -Lys-Z', -Cys-Z' (note that when a Cys moiety is also present in the 1 position of the polypeptide (i.e., X or AA1 is Cys), the resulting peptide can exist in the linear form or in the cyclic form), -Gly-Tyr-Z', and -Ala-Tyr-Z', wherein Z' is selected from the group consisting of —$CONH_2$, —CONHR, —COOH, —COOR, —$CONR_2$, —$CH_2OH$, and —$CH_2OR$, wherein R is as defined above;

and organic or inorganic addition salts of any of said polypeptides;

wherein the amino acid residue abbreviations used are in accordance with the standard peptide nomenclature:

Gly=Glycine
Tyr=L-Tyrosine
Ile=L-Isoleucine
Glu=L-Glutamic Acid
Thr=L-Threonine
Phe=L-Phenylalanine
Ala=L-Alanine
Lys=L-Lysine
Asp=L-Aspartic Acid
Cys=L-Cysteine
Arg=L-Arginine
Gln=L-Glutamine
Pro=L-Proline
Leu=L-Leucine
Met=L-Methionine
Ser=L-Serine
Asn=L-Asparagine
His=L-Histidine
Trp=L-Tryptophan
Val=L-Valine
DOPA=3,4-L-Dihydroxyphenylalanine
Met(O)=L-Methionine sulfoxide
iLys=$N^\epsilon$-Isopropyl-L-lysine
Orn=L-Ornithine
Sar=Sarcosine
Sar-ol=Sarcosine alcohol
Nle=L-Norleucine
D$^\alpha$Nal=$\alpha$-naphthyl-D-alanine
D$^\beta$Nal=$\beta$-naphthyl-D-alanine
Dermorphin=Either Try-DAla-Phe-Gly-Tyr-Pro-Ser-$NH_2$ or Try-DAla-Phe-Gly-Tyr-Hyp-Ser-$NH_2$
Gly-ol=2-Aminoethanol
Met(O)-ol=L-Methionine sulfoxide alcohol
Arg($NO_2$)=$N^g$-nitro-L-arginine All three letter amino acid abbreviations preceded by a "D" indicate the D-configuration of the amino acid residue.

While essentially stereochemically pure D or L amino acids are referred to throughout this specification, it is to be understood that mixtures of the D/L stereoisomers of the amino acid residues are also operable, while sometimes having a reduced level of biological activity as a function of the relative amount of the unspecified configuration which is present.

Group 3 polypeptides which may be combined with the novel Compound 1 and/or Compound 2 of the invention, or functional equivalents thereof, to provide a synergistic effect (optionally in further combination with a Group 2 polypeptide) are selected from any of polypeptides having the structure:

Tyr-DArg-Phe-$NH_2$;
Tyr-DAla-Phe-$NH_2$;
Tyr-DArg($NO_2$)-Phe-$NH_2$;
Tyr-DMet(O)-Phe-$NH_2$;
Tyr-DAlla-Phe-Gly-$NH_2$;
Tyr-DArg-Phe-Gly-$NH_2$
Tyr-DThr-Phe-Gly-$NH_2$;
Phe-DArg-Phe-Gly-$NH_2$;
Tyr-DArg-Phe-Sar;
Tyr-DAla-Gly-Phe-$NH_2$;
Tyr-DArg-Gly-Trp-$NH_2$;
Tyr-DArg($NO_2$)-Phe-Gly-$NH_2$;
Tyr-DMet(O)-Phe-Gly-$NH_2$;
Tyr-DArg-Phe-Gly-ol;
Tyr-DArg-Gly-(NMe)Phe-$NH_2$;
Try-DArg-Phe-Sar-ol
Tyr-DAla-Phe-Sar-ol
Tyr-DAla-Phe-Gly-Tyr-$NH_2$;
Gly-Tyr-DArg-Phe-Gly-$NH_2$;
Tyr-DThr-Gly-Phe-Thz-$NH_2$;
Gly-Tyr-DAla-Phe-Gly-$NH_2$;
Tyr-DAla-Phe-Gly-ol;
Tyr-DAla-Gly-(NMe)Phe-Gly-ol;
Tyr-DArg-Phe-Sar-$NH_2$;
Tyr-DAla-Phe-Sar-$NH_2$;
Tyr-DAla-Phe-Sar;
Tyr-DAla-Gly-(NMe)Phe-$NH_2$;
Sar-Tyr-DArg-Phe-Sar-$NH_2$;
Tyr-DCys-Phe-Gly-DCys-$NH_2$ (cyclic disulfide);
Tyr-DCys-Phe-Gly-DCys-$NH_2$ (free dithiol);
Tyr-DCys-Gly-Phe-DCys-$NH_2$ (cyclic disulfide);
Tyr-DCys-Gly-Phe-DCys-$NH_2$ (free dithiol);
Tyr-DAla-Phe-Gly-Tyr-Pro-Ser-$NH_2$;
Tyr-DAla-Phe-Sar-Tyr-Pro-Ser-$NH_2$;
Tyr-DAla-Phe-Sar-Phe-Pro-Ser-$NH_2$;
Tyr-DAla-Phe-Gly-Tyr-Hyp-Ser-$NH_2$;
Tyr-DAla-Phe-Sar-Tyr-Hyp-Ser-$NH_2$;
Tyr-DAla-Phe-Sar-Phe-Hyp-Ser-$NH_2$;
Tyr-DArg-Phe-Gly-Tyr-Hyp-Ser-$NH_2$;
Tyr-DArg-Phe-Sar-Tyr-Prop-Ser-$NH_2$;
Tyr-DArg-Phe-Sar-Tyr-Hyp-Ser-$NH_2$
Tyr-DArg-Phe-Gly-Tyr-Pro-Ser-$NH_2$; and organic or inorganic addition salts of any of said polypeptides of Group 3.

The Group 2 polypeptides preferred for combination with Compound 1 and/or Compound 2 or functional equivalents thereof (optionally in further combination with a Group 3 polypeptide) are the polypeptides having the structure:

Ala-His-DTrp-Ala-Trp-DPhe-Lys-Gly-Tyr-Z';
Ala-His-formyl)DTrp-Ala-Trp-Dphe-Lys-Z' (DTrp is formylated at the indole nitrogen);
Ala-His-DTrp-Ser-Trp-DPhe-Lys-Z';
Cys-Ala-His-DTrp-Ala-Trp-DPhe-Lys-Cys-Z' (cyclic disulfide);
Cys-Ala-His-DTrp-Ala-Trp-DPhe-Lys-Cys-Z' (free dithiol);
DOPA-Ala-His-DTrp-Ala-Trp-DPhe-Lys-Z';
His-DTrp-Ala-Trp-DPhe-Lys-Ala-Tyr-Z';
Lys-Ala-His-DTrp-Ala-Trp-DPhe-Lys-Z';
Phe-Ala-His-DTrp-Ala-Trp-DPhe-Lys-Z';
Tyr-Ala-Gly-Thr-Ala-His-DTrp-Ala-Trp-DPhe-Lys-Z';
Tyr-Ala-His-DTrp-Ala-Trp-DPhe-Lys-Z';
Tyr-DAla-Phe-Gly-Ala-His-DTrp-Ala-Trp-DPhe-Lys-Z';
Tyr-DAla-Gly-Phe-Ala-His-DTrp-Ala-Trp-DPhe-Lys-Z';

AA1-AA2-AA3-Ala-Trp-AA6-AA7-Z';
wherein
AA1 is selected from the group consisting of all naturally occurring L-amino acids, as well as Met(O), DOPA and Abu; and wherein Z' and R are as defined above;
AA2 is selected from the group consisting of His and 3(NMe)His (i.e., wherein the imidazole ring is methylated at the 3-position);
AA3 is selected from the group consisting of DTrp; 5-fluoro-D or D/LTrp; 6-fluoro-D or D/LTrp (i.e., wherein the indole ring is fluorinated at the 5- or 6-position); (formyl)DTrp (i.e., DTrp which is formylated at the indole nitrogen); *XTrp, wherein *XTrp is selected from the group consisting of the N-monomethylated DTrp isomers (i.e., ($N^{\alpha Me)DTrp}$ and (indole NME)DTrp); $D^{\alpha}$Nal; and $D^{\beta}$Nal;
AA6 is selected from the group consisting of DPhe and (NMe)DPhe;
AA7 is selected from the group consisting of Lys and iLys; and
organic or inorganic addition salts of any of said polypeptides.

The Group 3 polypeptides preferred for combination with Compound 1 and/or Compound 2 or functional equivalents thereof (optionally in further combination with a Group 2 polypeptide) are the polypeptides having the structure:
Tyr-DArg-Phe-$NH_2$;
Tyr-DArg($NO_2$)-Phe-$NH_2$;
Tyr-DMet(O)-Phe-$NH_2$;
Tyr-DAla-Phe-Gly-$NH_2$;
Tyr-DArg-Phe-Gly-$NH_2$;
Tyr-DArg-Phe-Sar;
Tyr-DAla-Gly-Phe-$NH_2$;
Tyr-DAla-Gly-(NMe)Phe-Gly-ol;
Tyr-DAla-Phe-Sar-$NH_2$;
Tyr-DAla-Phe-Sar-$NH_2$;
Tyr-DArg($NO_2$)-Phe-Gly-$NH_2$;
Tyr-DMet(O)-Phe-Gly-$NH_2$;
(NMe)Tyr-DArg-Phe-Sar-$NH_2$;
Tyr-DAla-Phe-Gly-ol;
Tyr-DAla-Phe-Gly-Tyr-$NH_2$;
Gly-Tyr-DArg-Phe-Gly-$NH_2$;
Gly-Tyr-DAla-Phe-Gly-$NH_2$;
Sar-Tyr-DArg-Phe-Sar-$NH_2$;
Tyr-DCys-Phe-Gly-DCys-$NH_2$ (cyclic disulfide);
Tyr-DCys-Phe-Gly-DCys-$NH_2$ (free dithiol)
Tyr-DCys-Gly-Phe-DCys-$NH_2$ (cyclic disulfide);
Tyr-DCys-Gly-Phe-DCys-$NH_2$ (free dithiol);
Tyr-DAla-Phe-Gly-Tyr-Pro-Ser-$NH_2$;
Tyr-DAla-Phe-Sar-Tyr-Pro-Ser-$NH_2$;
Tyr-DAla-Phe-Gly-Tyr-Hyp-Ser-$NH_2$;
Tyr-DArg-Phe-Gly-Tyr-Hyp-Ser-$NH_2$;
Tyr-DArg-Phe-Sar-Tyr-Pro-Ser-$NH_2$;
Tyr-Darg-Phe-Sar-Tyr-Hyp-Ser-$NH_2$;
Tyr-DArg-Phe-Gly-Tyr-Pro-Ser-$NH_2$;
and organic or inorganic addition salts of any of said polypeptides of Group 3.

The present invention also includes within its scope organic and inorganic addition salts comprising as an active ingredient:
a polypeptide selected from at least one of Compound 1, Compound 2 or functional equivalents thereof;
combinations of at least one of Compound 1, Compound 2, or functional equivalents thereof, with at least one of the Group 2 and Group 3 polypeptides, or functional equivalents thereof;
in association with a carrier, diluent, slow-release matrix or coating.

The organic or inorganic addition salts of the growth hormone releasing compounds and combinations thereof contemplated to be within the scope of the present invention include salts of such organic moieties as acetate, trifluoroacetate, oxalate, valerate, oleate, laurate, benzoate, lactate, tosylate, citrate, maleate, fumarate, succinate, tartrate, naphthalate, and the like; and such inorganic moieties as Group I (i.e., alkali metal salts), Group II (i.e., alkaline earth metal salts), ammonium and protamine salts, zinc, iron, and the like with counterions such as the chloride, bromide, sulfate, bisulfate, phosphate, borate and the like, as well as the organic moieties referred to above.

The invention is also concerned with a method of causing release and elevation of growth hormone levels in the blood of an animal, comprising administering an effective dose of Compound 1 and/or Compound 2, or a functional equivalent thereof, optionally as part of a combination comprising polypeptides selected from Compound 1 and /or Compound 2, or a functional equivalent thereof, along with at least one of the Group 2 and/or Group 3 polypeptides described above.

The amount of polypeptide or combination of polypeptides of the invention administered will vary depending upon the particular animal treated, its age and sex, the desired therapeutic effect, the route of administration and which polypeptides or combination of polypeptides are employed. In all instances, however, a dose effective to promote a release of growth hormone is used and ordinarily this dose level falls in the range of between about 0.1 $\mu$g to 10 mg/kg of body weight. When a combination of Compound 1 and/or Compound 2, or a functional equivalent thereof, and the Group 2 and/or Group 3 polypeptides are administered, they are employed in a ratio of proportions that provide synergistic results. These ratios will also vary depending upon whether Compound 1 or Compound 2, or a functional equivalent thereof is used, the particular Group 2 or Group 3 polypeptide or peptide selected from the combination, total dose employed, mode and protocol for administration, and the like. In general, the administration of combinations will allow the use of lower doses of each individual compounds to be used.

The compounds of this invention can be administered by a variety of techniques as can be readily determined by those of skill in the art, e.g., oral; parenteral; intramuscular (i.m.), intraperitoneal (i.p.), intravenous (i.v.) or subcutaneous (s.c.) injection; nasal; vaginal; rectal; sublingual; implant or transdermal routes of administration and can be formulated in dose forms appropriate for each route of administration.

Suitable solid dose forms for oral administration include, for example, capsules, tablets, pills, powders and granules. In such solid dose forms, the active compound can be mixed with at least one inert carrier such as sucrose, lactose, or starch. Such dose forms can also comprise, as is normal practice, additional substances other than inert diluents, e.g., lubricating agents such as magnesium stearate. In the case of capsules, tablets and pills, the dose forms can also comprise buffering agents. Tablets and pills can additionally be prepared with enteric coatings.

Suitable liquid dose forms for oral administration include, for example, emulsions, solutions, suspensions, syrups, the elixirs containing inert diluents commonly used in the art, such as water. Besides, such inert diluents, compositions can also include adjuvants, such as wetting agents, emulsifying and suspending agents, and sweetening, flavoring, colorizing and perfuming agents.

Preparations according to this invention for parental administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria-retaining filter, by incorporating sterilizing agents into the compositions, by irradiating the compositions, or by heating the compositions. They can also be manufactured in a medium of sterile water, or some other sterile injectable medium immediately before use.

The following examples are given to further illustrate the present invention.

EXAMPLE 1

Synthesis of Compound
1-Tyr-Ala-Asp-Ala-Ile-Phe-Thr-Asn-Cys-Tyr-Arg-Lys-Val-Leu-Cys-Gln-Leu-Ser-Ala-Arg-Lys-Leu-Leu-Gln-Asp-Ile-Nle-Ser-Arg-$NH_2$ (free dithiol)

Compound 1 can be prepared as follows:

Para-methylbenzylhydrylamine hydrochloride (p-Me-BHA.HCl) resin is placed in a reaction vessel on a commercially available automated peptide synthesizer. The resin can be substituted with free amine up to a loading of about 2.5 mmoles per gram. The compounds are prepared by coupling individual amino acids starting at the carboxy terminus of the peptide sequence using an appropriate activating agent, such as N,N'-dicyclohexylcarbodiimide (DCC). The alpha-amino group of individual amino acids are protected as the tertiary-butyloxycarbonyl derivative (t-Boc) and the reactive side chain functionalities are protected as outlined in Table 1.

TABLE 1

Side Chain Protecting Groups Suitable for Solid Phase Peptide Synthesis

| | |
|---|---|
| Arginine: | $N^g$—Tosyl |
| Aspartic Acid: | O—Benzyl |
| Cysteine: | S—para-Methylbenzyl |
| Glutamic Acid: | O—Benzyl |
| Histidine: | $N^{im}$—Tosyl |
| Lysine: | $N^\epsilon$—2,4-Dichlorobenzyloxycarbonyl |
| Methionine: | S—Sulfoxide |
| Serine: | O—Benzyl |
| Threonine: | O—Benzyl |
| Tryptophan: | $N^{in}$—Formyl |
| Tyrosine: | O—2,6-Dichlorobenzyl |

Prior to incorporation of the initial amino acid the resin is agitated three times (about one minute each) with dichloromethane ($CH_2Cl_2$); about 10 ml/gm of resin), neutralized with three agitations (about two minutes each) of N,N'-diisopropylethylamine (DIEA) in dichloromethane (10:90; about 10 ml/gm of resin) and agitated three times (about one minute each) with dichloromethane (about 10 ml/gm of resin). The initial and each subsequent amino acids are coupled to the resin using a preformed symmetrical anhydride using about 3.0 times the total amount of the binding capacity of the resin of a suitably protected amino acid and about 1.5 times the total amount of the binding capacity of the resin of DCC in an appropriate amount of dichloromethane. For amino acids with a low dichloromethane solubility, N,N-dimethylformamide (DMF) is added to achieve a homogenous solution. Generally, the symmetrical anhydride is prepared up to 30 minutes prior to introduction into the reaction vessel at room temperature or below. The N,N'-dicyclohexylurea that forms upon preparation of the symmetrical anhydride can be removed via gravity filtration of the solution into the reaction vessel. Progress of the coupling of the amino acid to the resin is commonly monitored via a color test using reagents such as ninhydrin which reacts with primary and secondary amines. Upon complete coupling of the protected amino acid to the resin (>99%), the alpha amine protecting group is removed by a series of acidic reagents. A commonly used reagent consists of a solution of trifluoroacetic acid (TFA), and anisole in dichloromethane (45:2:53). The complete procedure for incorporation of each individual amino acid residue onto the resin is outlined in Table 2.

TABLE 2

Procedure for Incorporation of Individual Amino Acids onto a Resin

| | Reagent | Agitations | Time/Agitation |
|---|---|---|---|
| 1. | Dichloromethane | 3 | 1 min. |
| 2. | TFA, Anisole, Dichloromethane (45:2:53) | 1 | 2 min. |
| 3. | TFA, Anisole, Dichloromethane (45:2:53) | 1 | 20 min. |
| 4. | Dichloromethane | 3 | 1 min. |
| 5. | DIEA, Dichloromethane (10:90) | 3 | 2 min. |
| 6. | Dichloromethane | 3 | 1 min. |
| 7. | Preformed symmetrical anhydride | 1 | 15-120 min.* |
| 8. | Dichloromethane | 3 | 1 min. |
| 9. | iso-Propanol | 3 | 1 min. |
| 10. | Dichloromethane | 3 | 1 min. |
| 11. | Monitor progress of the coupling reaction** | | |
| 12. | Repeat Steps 1-12 for Each Individual Amino Acid | | |

*Coupling time depends upon the individual amino acid.
**The extent of coupling is generally monitored by a color test. If the coupling is incomplete, the same amino acid is recoupled by repeating Steps 7-11. If the coupling is complete the next amino acid can be coupled.

To prepare Compounds 1 and 2 the following suitably protected (see Table 1) amino acids are coupled to the p-Me-BHA resin in the following order: Arg, Ser, Nle, Ile, Asp, Gln, Leu, Leu, Lys, Arg, Ala, Ser, Leu, Gln, Cys, Leu, Val, Lys, Arg, Tyr, Cys, Asn, Thr, Phe, Ile, Ala, Asp, Ala, Tyr. Following coupling of the final amino acid, the final alpha amino protecting group is removed and the resin dried. The peptide and all protecting groups are removed from the resin using anhydrous hydrogen fluoride (HF) in a commercially available Teflon HF-reaction apparatus. The HF is dried with cobalt trifluoride after being distilled from the carrier cylinder into a Teflon holding reservoir under high vacuum. The HF is then distilled into the Teflon reaction vessel (about 10 ml per gram of resin) containing the peptide resin and scavengers, such as; anisole and/or 1,2-ethanedithiol, and the like. The solution is stirred for 45 to 60 minutes at 0° C., after which the HF can be removed under high vacuum. The remaining organic scavengers are removed from the resin by washing with an appropriate non-polar organic solvent, such as ethyl ether or ethyl acetate. The peptide is extracted from the resin with 30% aqueous acetic acid and obtained in powder form after freeze drying. Compound 1 is obtained in pure form by either low or high pressure liquid chromatography.

EXAMPLE 2

Synthesis of Compound 2

Example 1 is repeated to obtain the free dithiol (Compound 1), which is subjected to oxidation to provide the cyclic disulfide (Compound 2) by the following procedure. A solution (0.1–1000 mg per liter) of the free dithiol is prepared in distilled water. The pH is adjusted to be basic (about pH 9). At this point a dilute solution of potassium ferricyanide (0.005–1.0N) in water can be added until a yellow tinge to the solution is obtained and is maintained for about one hour with continuous titration and stirring. The oxidation can be quenched by adjusting to an acidic pH (about 4) and excess ferro and ferricyanide are removed by the addition of a large excess of a weakly basic gel-type polystyrene polyamine ion exchange resin, such as Rexyn (Cl$^-$ form) 203 or Bio-Rad AG3-X4A. The resin can be stirred overnight and removed by gravity filtration, after which the peptide can be obtained in powder form by freeze drying. Compound 2 can be obtained in pure form by either low or high pressure liquid chromatography.

EXAMPLE 3

In Vivo GH Release in Rats

Immature female Sprague-Dawley rats were obtained from the Charles River Laboratories (Wilmington, Mass.). After arrival they were housed at 25° C. with 14:10 hour light:dark cycle. Water and Purina rat choow were availablle ad libitum. Pups were kept with their mothers until 21 days of age.

Normal saline with 0.1% gelatin was the vehicle for s.c. and i.v. injections of Compounds 1 and 2. The unanesthetized rats, weighing 55–65 grams, were injected i.v. with 0.2 ml solution via the tail vein. All animals were sacrificed by quillotine 10 minutes after the final test injection unless specified otherwise. Trunk blood for growth hormone (GH) determinations was collected following decapitation. The blood was allowed to clot, centrifuged and the serum separated from the clot. Serum was kept frozen until the day of sampling for radioimmunoassay (RIA) of growth hormone levels according to the following procedure, as developed by the National Institute of Arthritis, Diabetes and Digestive and Kidney Diseases (NIADDK).

Reagents are generally added to the RIA analysis tubes at a single sitting, at refrigerator temperature (about 4° C.) in the following sequence:
(a) buffer,
(b) "cold" (i.e., non-radioactive) standard or unknown serum sample to be analyzed,
(c) radio-iodinated growth hormone antigen, and
(d) growth hormone antiserum.
Reagent addition is generally carried out so that there is achieved a final RIA tube dilution in the range of about 1:10,000 up to 1:500,000 (antiserum to total liquid volume; vol:vol).

The mixed reagents are then typically incubated at room temperature (about 25° C.) for about 24 hours prior to addition of a second antibody (e.g., goat or rabbit anti-monkey gamma globulin serum) which binds to and cause precipitation of the complexed growth hormone antiserum. Precipitated contents of the RIA tubes are then analyzed for the number of counts in a specified period of time in a gamma scintillation counter. A standard curve is prepared by plotting number of radioactive counts as a function of growth hormone (GH) level. GH levels of unknowns are then determined by reference to the standard curve.

Serum GH was measured by RIA with reagents provided by the National Hormone and Pituitary Program. Serum levels are recorded in ng/ml in terms of the rat GH standard with 0.61 IU/mg. Data is recorded as the mean ± standard error of the mean (SEM). Statistical analysis was performed with student's t-test.

The results are shown in Table 3.

TABLE 3

| Compound | Amount μg | Control, ng/ml | GH Release, (ng/ml) |
|---|---|---|---|
| A$^{(a)}$ | 1 | 2.0 ± 0.2 | 64 ± 16 |
| A | 3 | 2.0 ± 0.2 | 105 ± 23 |
| A | 10 | 9.0 ± 1.0 | 114 ± 21 |
| 2$^{(b)}$ | 3 | 14.0 ± 1.0 | 62 ± 8 |
| 2 | 10 | 14.0 ± 1.0 | 99 ± 11 |
| 2 | 30 | 14.0 ± 1.0 | 132 ± 24 |
| 1$^{(c)}$ | 10 | 13.0 ± 2.0 | 145 ± 41 |
| 1 | 30 | 13.0 ± 2.0 | 151 ± 33 |
| 1 | 100 | 13.0 ± 2.0 | 374 ± 94 |

$^{(a)}$Compound A is [Nle$^{27}$]—hGRF(1-29)—NH$_2$ which is Tyr—Ala—Asp—Ala—Ile—Phe—Thr—Asn—Ser—Tyr—Arg—Lys—Val—Leu—Gly—Gln—Leu—Ser—Ala—Arg—Lys—Leu—Leu—Gln—Asp—Ile—Nle—Ser—Arg—NH$_2$
$^{(b)}$Compound 2 is [Cys$^9$, Cys$^{15}$, Nle$^{27}$]—hGRF(1-29)—NH$_2$ which is Tyr—Ala—Asp—Ala—Ile—Phe—Thr—Asn—Cys—Tyr—Arg—Lys—Val—Leu—Cys—Gln—Leu—Ser—Ala—Arg—Lys—Leu—Leu—Gln—Asp—Ile—Nle—Ser—Arg—NH$_2$ (cyclic disulfide)
$^{(c)}$Compound 1 is [Cys$^9$, Cys$^{15}$, Nle$^{27}$]—hGRF(1-29)—NH$_2$ which is Tyr—Ala—AsP—Ala—Ile—Phe—Thr—Asn—Cys—Tyr—Arg—Lys—Val—Leu—Cys—Gln—Leu—Ser—Ala—Arg—Lys—Leu—Leu—Gln—Asp—Ile—Nle—Ser—Arg—NH$_2$ (linear dithiol)

In Table 3, Compounds 1 and 2 are shown to cause the release of growth hormone when administered to rats via i.v. injection. Both of the compounds are highly active and are shown to have the potencies similar to Compound A. This data shows that Compound 2 is a fully active cyclic analog of human growth releasing factor ([Nle$^{27}$]-hGRF(1-29)-NH$_2$; and, to the best of our knowledge, is the first highly active cyclic analog ever prepared.

EXAMPLE 4

Compound 1 and Compound 2 of Examples 1 and 2, respectively, were each combined with the Group 2 and/or Group 3 polypeptides identified in Table 4 below and in the proprotions shown. The combinations were then tested for GH release in rats by the same procedure set forth in Example 3. The synergistic effects of the combinations is shown in Table 4.

TABLE 4

In Vivo Synergistic Effects of Invention & Structurally Similar Compounds With Compound B[d] (Group 3) and Compound C[e] (Group 2) in Rats

| Column A, Compound | Dose | Control | GH Release by Compound in Column A | Compound B, 30 μg | GH Release of Compound in Column A & 30 μg Compound B | Compound C, -μg | Compound C and Compound in Column A | GH Release of Compound in Column A & 30 μg Compound B & 10 μg Compound C |
|---|---|---|---|---|---|---|---|---|
| A[a] | 10 | 14 ± 1 | 115 ± 27 |  | 1803 ± 224 |  |  |  |
| A | 10 | 10 ± 1 | 103 ± 16 | 131 ± 44 | 1666 ± 137 |  |  |  |
| A | 10 | 12 ± 2 | 94 ± 22 | 107 ± 42 | 2332 ± 348 |  |  |  |
| A | 10 | 13 ± 2 | 131 ± 51 | 229 ± 26 | 1744 ± 200 |  |  | 4889 ± 721 |
| 1[c] | 10 | 13 ± 2.0 | 145 ± 41 | 229 ± 26 | 3314 ± 275 |  |  | 4947 ± 366 |
| 1 | 30 | 13 ± 2.0 | 151 ± 33 | 229 ± 26 | 2875 ± 472 |  |  |  |
| 1 | 100 | 13 ± 2.0 | 374 ± 94 | 229 ± 26 | 2328 ± 297 |  |  |  |
| 1 | 10 | 10 ± 0.2 | 77 ± 10 | 274 ± 68 | 2078 ± 395 |  |  |  |
| 2[b] | 3 | 14 ± 1.0 | 62 ± 8 | 121 ± 50 | 1689 ± 264 |  |  |  |
| 2 | 10 | 14 ± 1.0 | 99 ± 11 | 121 ± 50 | 3733 ± 515 |  |  |  |
| 2 | 30 | 14 ± 1.0 | 132 ± 24 | 121 ± 50 | 2652 ± 560 |  |  |  |
| 2 | 10 | 10 ± 0.2 | 105 ± 29 | 274 ± 68 | 2241 ± 323 |  |  |  |

[a]Compound A is [Nle$^{27}$]—GRF(1-29)—NH$_2$ which is Tyr—Ala—Asp—Ala—Ile—Phe—Thr—Asn—Ser—Tyr—Arg—Lys—Val—Leu—Gly—Gln—Leu—Ser—Ala—Arg—Lys—Leu—Leu—Gln—Asp—Ile—Nle—Ser—Arg—NH$_2$
[b]Compound 2 is [Cys$^9$, Cys$^{15}$, Nle$^{27}$]—GRF(1-29)—NH$_2$ which is Tyr—Ala—Asp—Ala—Ile—Phe—Thr—Asn—Cys—Tyr—Arg—Lys—Val—Leu—Cys—Gln—Leu—Ser—Ala—Arg—Lys—Leu—Leu—Gln—Asp—Ile—Nle—Ser—Arg—NH$_2$ (cyclic disulfide)
[c]Compound 1 is [Cys$^9$, Cys$^{15}$, Nle$^{27}$]—GRF(1-29)—NH$_2$ which is Tyr—Ala—Asp—Ala—Ile—Phe—Thr—Asn—Cys—Tyr—Arg—Lys—Val—Leu—Cys—Gln—Leu—Ser—Ala—Arg—Lys—Leu—Leu—Gln—Asp—Ile—Nle—Ser—Arg—NH$_2$ (linear dithiol)
[d]Compound B is Tyr—DArg—Phe—Gly—NH$_2$
[e]Compound C is Ala—His—DTrp—Ala—Trp—DPhe—Lys—NH$_2$ In Table 4, Compounds 1 and 2 are shown to act synergistically with the Group 3 Compound B (Tyr-DArg-Phe-Gly-NH$_2$). In every case, for Compounds 1 and 2 when the amount of GH released by the individual compound is added to the amount of GH released by Compound B when given alone, the result is far less than the amount of GH released when the two compounds have been administered to the rat either simultaneously, or at different locations on the rat. Thus, synergism is seen for all such combinations.

The invention has been described in detail with particular reference to preferred embodiments threof, but it will be understood that variations and modifications can be effected within the spirit and scope of the invention.

We claim:

1. A polypeptide selected from the group consisting of:

Compound 1
Tyr—Ala—Asp—Ala—Ile—Phe—Thr—Asn—Cys—Tyr—Arg—

Lys—Val—Leu—Cys—Gln—Leu—Ser—Ala—Arg—Lys—Leu—

Leu—Gln—Asp—Ile—Nle—Ser—Arg—NH$_2$ (free dithiol), and organic or inorganic addition salts thereof; and Compound 2
Tyr—Ala—Asp—Ala—Ile—Phe—Thr—Asn—Cys—Tyr—Arg—

Lys—Val—Leu—Cys—Gln—Leu—Ser—Ala—Arg—Lys—Leu—

Leu—Gln—Asp—Ile—Nle—Ser—Arg—NH$_2$ (cyclic disulfide),

2. A pplypeptide according to claim 1 wherein the polypeptide is Compound 1, thereof.

3. A polypeptide according to claim 1 wherein the polypeptide has the structure:

Tyr—Ala—Asp—Ala—Ile—Phe—Thr—Asn—Cys—Tyr—

—Arg—Lys—Val—Leu—Cys—Gln—Leu—Ser—Ala—Arg—

—Lys—Leu—Leu—Gln—Asp—Ile—Nle—Ser—Arg—NH$_2$ (free dithiol).

4. A polypeptide according to claim 1 wherein the polypeptide is Compound 2, or organic or inorganic addition salts thereof.

5. A polypeptide according to claim 1 wherein the polypeptide has the structure:

Tyr—Ala—Asp—Ala—Ile—Phe—Thr—Asn—Cys—Tyr—

—Arg—Lys—Val—Leu—Cys—Gln—Leu—Ser—Ala—Arg—

—Lys—Leu—Leu—Gln—Asp—Ile—Nle—Ser—Arg—NH$_2$ (cyclic disulfide).

6. A composition in accordance with claim 1 further comprising a carrier or diluent.

7. A composition according to claim 6 wherein the active ingredient is Compound 1.

8. A composition according to claim 6 wherein the active ingredient is Compound 2.

9. A composition according to claim 6 wherein the active ingredient is a mixture of Compound 1 and Compound 2.

10. A method of promoting the release of growth hormone in an animal which comprises administering to said animal an effective amount of the polypeptide of claim 1.

11. A method according to claim 10 wherein the polypeptide is Compound 1.

12. A method according to claim 10 wherein the polypeptide is Compound 2.

* * * * *

UNITED STATES PATENT AND TRADEMARK OFFICE
CERTIFICATE OF CORRECTION

PATENT NO. : 4,880,777

DATED : November 14, 1989

INVENTOR(S) : Frank A. Momany

It is certified that error appears in the above-identified patent and that said Letters Patent is hereby corrected as shown below:

Claim 1, Column 13, line 61, please insert after "(cyclic disulfide)," ---and organic or inorganic addition salts thereof.---

Claim 2, Column 13, line 64, after "Compound 1," and before "thereof." please insert ---or organic or inorganic addition salts---.

Signed and Sealed this

Twenty-third Day of October, 1990

Attest:

HARRY F. MANBECK, JR.

*Attesting Officer*     Commissioner of Patents and Trademarks